United States Patent
Amon et al.

(10) Patent No.: US 10,844,851 B2
(45) Date of Patent: Nov. 24, 2020

(54) INFUSION DEVICE COMPRISING A WOBBLING DEVICE FOR ACTING ONTO A PUMP MODULE

(71) Applicant: Fresenius Vial SAS, Brézins (FR)

(72) Inventors: Barbara Amon, Idstein (DE); Michael Becker, Knittlingen (DE)

(73) Assignee: Fresenius Vial SAS, Brézins (FR)

(*) Notice: Subject to any disclaimer, the term of this patent is extended or adjusted under 35 U.S.C. 154(b) by 245 days.

(21) Appl. No.: 15/579,470

(22) PCT Filed: Apr. 22, 2016

(86) PCT No.: PCT/EP2016/058975
§ 371 (c)(1),
(2) Date: Dec. 4, 2017

(87) PCT Pub. No.: WO2016/198197
PCT Pub. Date: Dec. 15, 2016

(65) Prior Publication Data
US 2018/0149149 A1  May 31, 2018

(30) Foreign Application Priority Data
Jun. 11, 2015 (EP) ..................................... 15305892

(51) Int. Cl.
*F04B 43/12* (2006.01)
*A61M 5/142* (2006.01)
(Continued)

(52) U.S. Cl.
CPC ......... *F04B 43/1207* (2013.01); *A61M 5/142* (2013.01); *A61M 5/14232* (2013.01);
(Continued)

(58) Field of Classification Search
CPC ...... F04B 43/12; F04B 43/1207; F04B 43/14; F04B 43/082; A61M 5/14232; F04C 9/005
See application file for complete search history.

(56) References Cited

U.S. PATENT DOCUMENTS 2,841,091 A * 7/1958 Schaurte ................. F04B 43/14
417/477.5
2,958,294 A * 11/1960 Johnson ................ F04B 43/082
418/45
(Continued)

FOREIGN PATENT DOCUMENTS

DE  32 27 051 A1  2/1984
FR  2 690 621  11/1993

OTHER PUBLICATIONS

International Search Report and Written Opinion, counterpart International Appl. No. PCT/EP2016/058975, dated Jul. 26, 2016 (10 pages).

*Primary Examiner* — Peter J Bertheaud
(74) *Attorney, Agent, or Firm* — Cook Alex Ltd.

(57) ABSTRACT

An infusion device (3) comprises a housing element (30) having a receptacle (301) for receiving a pump module (1), and a pump actuation mechanism (2) having a wobbling device (20) arranged on the housing element (30) and a drive shaft (21) being rotatable about a rotational axis (A). The wobbling device (20) is actuatable, by rotating the drive shaft (21) about the rotational axis (A), to perform a tumbling motion with respect to the receptacle (300) for acting onto the pump module (1) received in the receptacle (300) in order to pump a fluid through the pump module (1). Herein, the wobbling device (20) is displaceable along at least one direction (X, Y) transverse to the rotational axis (A) with respect to the receptacle (300). In this way an infusion device is provided which in an easy and cost- (Continued)

efficient manner allows for improving the positional accuracy of the pump module with respect to the wobbling device of the pump actuation mechanism upon arranging the pump module on the receptacle of the housing element.

14 Claims, 5 Drawing Sheets

(51) Int. Cl.
  *F04B 43/14* (2006.01)
  *F04B 43/08* (2006.01)
  *F04C 9/00* (2006.01)
  *A61M 5/168* (2006.01)

(52) U.S. Cl.
  CPC ............ *F04B 43/082* (2013.01); *F04B 43/12* (2013.01); *F04B 43/14* (2013.01); *F04C 9/005* (2013.01); *A61M 2005/16868* (2013.01); *A61M 2005/16872* (2013.01)

(56) References Cited

U.S. PATENT DOCUMENTS

| | | | | |
|---|---|---|---|---|
| 3,669,578 A | * | 6/1972 | Nameny | F04B 43/14 418/45 |
| 4,483,666 A | | 11/1984 | Schubert et al. | |
| 5,458,469 A | * | 10/1995 | Hauser | F04B 43/1207 417/474 |
| 6,296,460 B1 | * | 10/2001 | Smith | F04B 43/14 417/475 |
| 7,393,189 B2 | * | 7/2008 | Davis | A61M 1/0058 417/477.12 |
| 8,784,079 B2 | * | 7/2014 | Becker | A61M 5/1413 417/476 |
| 9,062,672 B2 | * | 6/2015 | Becker | A61M 5/1413 |
| 9,062,673 B2 | * | 6/2015 | Becker | A61M 5/1413 |
| 9,157,430 B2 | * | 10/2015 | Becker | A61M 5/1413 |
| 9,470,220 B2 | * | 10/2016 | Becker | A61M 5/1413 |
| 2012/0207635 A1 | | 8/2012 | Becker | |

* cited by examiner

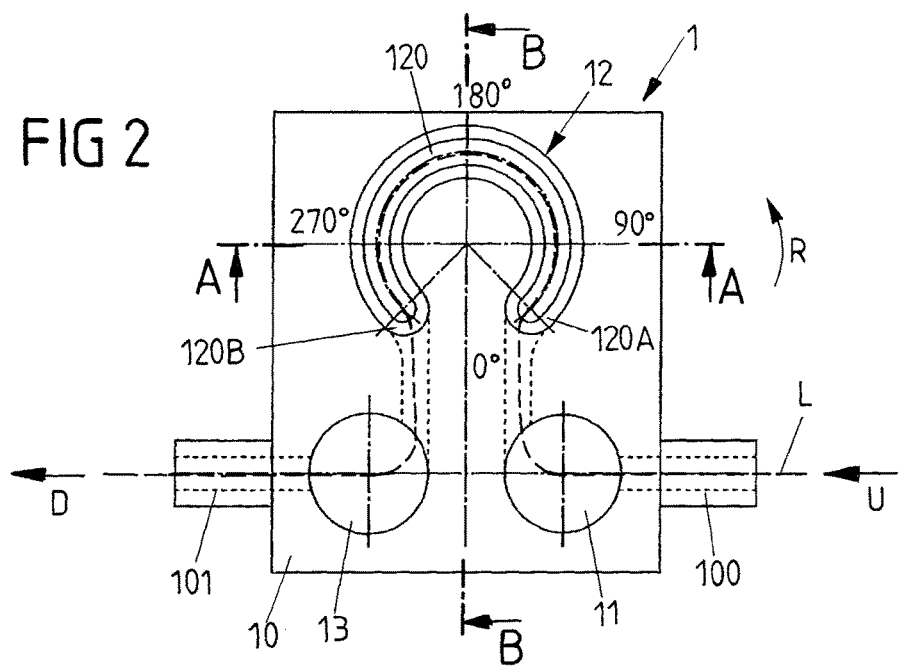
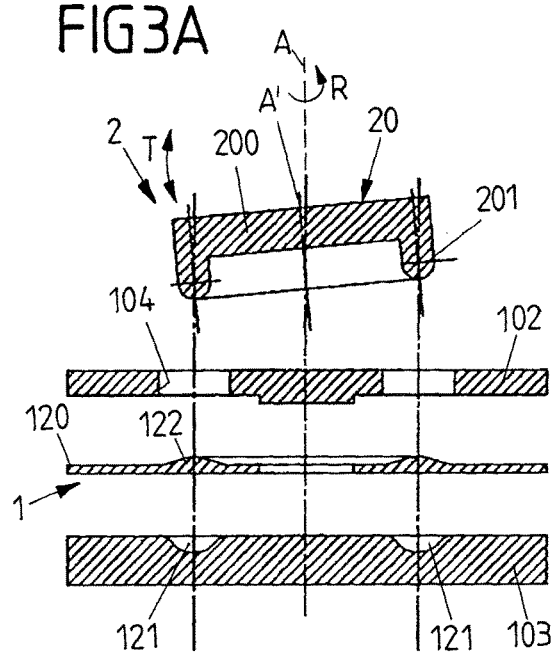
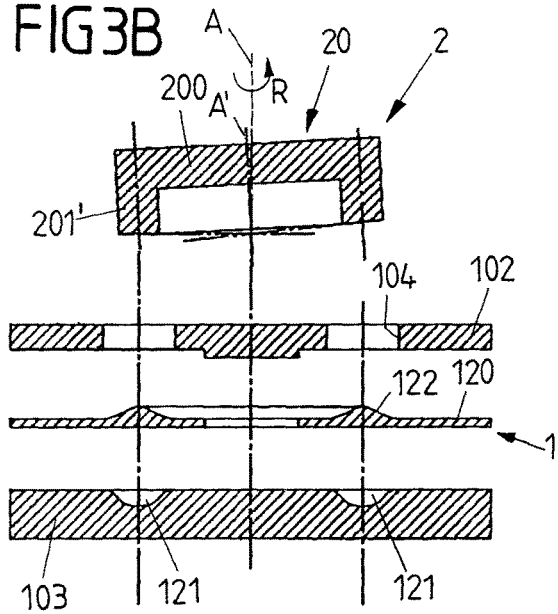
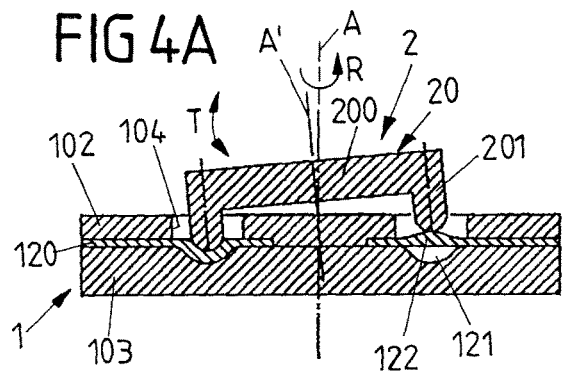
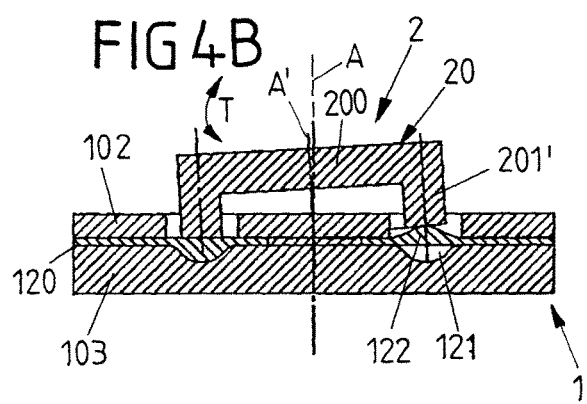

INFUSION DEVICE COMPRISING A WOBBLING DEVICE FOR ACTING ONTO A PUMP MODULE

The present application is a U.S. National Stage of PCT International Patent Application No. PCT/EP2016/058975, filed Apr. 22, 2016, which claims priority to EP Application No. 15305892, filed Jun. 11, 2015, both of which are hereby incorporated herein by reference:

DESCRIPTION

The invention relates to an infusion device according to the preamble of claim 1.

An infusion device of this kind comprises a housing element having a receptacle for receiving a pump module and a pump actuation mechanism having a wobbling device arranged on the housing element and a drive shaft being rotatable about a rotational axis. The wobbling device is actuatable, by rotating the drive shaft about the rotational axis, to perform a tumbling motion about the rotational axis with respect to the receptacle for acting onto the pump module received in the receptacle in order to pump a fluid through the pump module.

An infusion device as generally concerned herein is for example described in US 2012/0207635 A1.

The infusion device is constituted as a peristaltic (volumetric) infusion pump. The pump module may, for example, have the shape of a disposable pump module which can be attached to the receptacle of the infusion device. By attaching the pump module to the receptacle it is brought into engagement with the wobbling device of the pump actuation mechanism such that, in operation of the infusion device, the wobbling device may act onto a flexible wall section of the pump module in order to locally depress it in a revolving fashion and in this way pump a fluid through a pump channel of the pump module. During operation the wobbling device hence depresses the flexible wall section at a depression location, wherein by actuating the wobbling device the depression location moves along the channel length of the pump channel and in this way peristaltically pumps a fluid through the pump channel.

For attaching the pump module to the infusion device it is inserted into the receptacle of the housing element such that the wobbling device of the pump actuation mechanism may act onto the pump module. The receptacle herein may for example be formed as a reception opening into which the pump module may be inserted such that, in an inserted state, it is held in the receptacle in a form locking manner. Since the wobbling device is arranged on the receptacle at a defined position, the pump module is brought into a defined spatial relation with the wobbling device when arranging the pump module in the receptacle. In this way, the wobbling device is for example brought into abutment with a flexible wall section in the shape of a membrane of the pump module such that it may peristaltically depress the flexible wall section in order to pump a fluid through a pump channel of the pump module during operation of the infusion device.

However, the pump module, the receptacle and the wobbling device may be subject to tolerances. The position of the pump module with respect to the wobbling device hence may deviate from an ideal, nominal position which the pump module should assume in order to achieve a pumping action with an accurate flow rate. If there is a lateral mismatch between the wobbling device and the pump module (transverse to the rotational axis of the drive shaft driving the wobbling device), this may affect the flow rate accuracy because the stroke volume (corresponding to the volume of fluid pumped through the pump channel of the pump module during one pump cycle) may differ from a reference, nominal stroke volume, causing the actual flow rate to differ from a desired, nominal flow rate.

There hence is a desire to be able to correct for a lateral mismatch in the position of the pump module with respect to the wobbling device in order to avoid a reduced flow rate accuracy.

It is an object of the instant invention to provide an infusion device which in an easy and cost-efficient manner allows for improving the positional accuracy of the pump module with respect to the wobbling device of the pump actuation mechanism upon arranging the pump module on the receptacle of the housing element.

This object is achieved by means of an infusion device comprising the features of claim 1.

Accordingly, the wobbling device is displaceable along at least one direction transverse to the rotational axis with respect to the receptacle.

Because the wobbling device is displaceable in a direction transverse to the rotational axis with respect to the receptacle, lateral tolerances in the position in-between the wobbling device and the pump module may be corrected. When the pump module is attached to the housing element by placing it on the receptacle, the lateral position of the wobbling device may be adjusted with respect to the pump module such that the wobbling device may assume an optimum position with respect to the pump module for acting onto the pump module in order to pump a fluid through the pump module. Because the lateral position of the wobbling device with respect to the pump module can laterally be adjusted, inaccuracies in the stroke volume may be avoided or at least reduced and hence the flow rate accuracy of the infusion device may be improved.

Within the context of the instant text the displaceability of the wobbling device in a direction transverse to the rotational axis shall refer to a lateral change of position of the wobbling device as a whole, disregarding the tumbling motion of the wobbling device during operation of the infusion device. If the wobbling device is laterally mounted on the drive shaft, the lateral displaceability of the wobbling device will include a displaceability of the lateral position of the rotational axis with respect to the receptacle.

Because the wobbling device is displaceable along at least one direction transverse to the rotational axis, its lateral position with respect to the pump module is adjustable such that the wobbling device may assume an optimum lateral position with respect to the pump module during operation of the infusion device. In addition, the wobbling device beneficially is displaceable longitudinally along the rotational axis with respect to the receptacle, such that also the longitudinal position of the wobbling device is adjustable.

Herein, in one embodiment, the wobbling device is elastically pretensioned with respect to the housing element of the infusion device along the rotational axis in a direction pointing towards the receptacle, such that the wobbling device is brought into abutment with the pump module when placing the pump module in or on the receptacle. The abutment herein occurs under a pretension such that the wobbling device is tensioned towards for example a flexible wall section of the pump module. This may beneficially lead to a pre-loading of the flexible wall section of the pump volume in that in any case the wobbling device abuts the flexible wall section along the entire channel length. Herein, dependent on the position of the wobbling device the flexible wall section is only locally depressed such that the height of the pump channel at its depression location is reduced to a minimum and the pump channel is squeezed off at the depression location.

However, also at other locations along the pump channel the wobbling device abuts the flexible wall section such that the flexible wall section is preloaded along the entire channel length.

The wobbling device, in one embodiment, is mounted on the drive shaft via a first bearing such that the wobbling device is actuated to perform a tumbling motion when rotating the drive shaft. The wobbling device, during operation of the infusion device, performs a tumbling motion, but is not rotated about the rotational axis. The drive shaft, in contrast, is rotated about the rotational axis and acts onto the wobbling device such that the wobbling device tumbles about the rotational axis. For this to take place, the wobbling device is mounted on the drive shaft such that the drive shaft may be rotated with respect to the wobbling device. Because the bearing axis (corresponding to a tumbling axis) is at a skew angle with respect to the rotational axis, the wobbling device tumbles about the rotational axis upon rotating the drive shaft about its rotational axis.

The drive shaft in turn, in one embodiment, is mounted on a carrier element via a second bearing such that the drive shaft is rotatable with respect to the carrier element about the rotational axis. In that the carrier element is mounted on the housing element such that the carrier element is displaceable along at least one direction transverse to the rotational axis with respect to the housing element, the wobbling device mounted on the drive shaft is transversely displaceable with respect to the receptacle. The wobbling device hence, in this embodiment, is not displaceable with respect to the drive shaft, but the carrier element is displaceable together with the drive shaft and the wobbling device mounted on the drive shaft, such that a displacing of the carrier element in a direction transverse to the rotational axis leads to a displacement of the wobbling device with respect to the receptacle.

In principle, the carrier element may be mounted and connected to the housing element in different ways such that it is displaceable transversely to the rotational axis of the drive shaft. In one embodiment, the carrier element is connected to the housing element via an elastically deformable connection element, for example in the shape of a connection plate connecting the carrier element to the housing element. By means of the connection element the carrier element is held on the housing element, wherein the connection element may be deformed in order to displace the carrier element by at least some margin along a plane transverse to the rotational axis.

The displacement of the carrier element herein may beneficially occur against an elastic tensioning of the connection element. The displacing of the carrier element may take place dynamically upon placing the pump module in or on the receptacle for operation of the infusion device.

In one embodiment, the carrier element may be elastically pretensioned with respect to the housing element along the rotational axis. Via the elastic pretensioning of the carrier element, for example by means of a suitable spring element, hence the wobbling device is pretensioned towards the pump module for a suitable abutment with the pump module.

The wobbling device, in one embodiment, comprises a wobbling disc extending along a plane transverse to a tumbling axis, wherein the tumbling axis is arranged at a skew angle with respect to the rotational axis and tumbles about the rotational axis when the wobbling device is driven by the drive shaft. The wobbling disc may be mounted on the drive shaft by means of a suitable bearing, wherein the bearing axis (i.e. the axis about which the wobbling device is rotatable with respect to the drive shaft) corresponds to the tumbling axis and is arranged at a skew angle with respect to the rotational axis of the drive shaft. When driving the wobbling device by means of the drive shaft, the wobbling device remains rotationally fixed, but tumbles about the rotational axis of the drive shaft.

In order to act onto the pump module, a protrusion may be arranged on the wobbling device protruding from the wobbling device along the tumbling axis. Via the protrusion the wobbling device may act onto a flexible wall section of the pump module, for example a membrane confining the pump channel of the pump module for locally depressing the pump channel in a revolving fashion for peristaltically pumping a fluid through the pump channel.

The wobbling device, in one embodiment, may be constituted to self-align itself with respect to the pump module in a lateral direction with respect to the rotational axis of the drive shaft. The self-alignment for example may take place in that the wobbling device, when depressing the flexible wall section of the pump module, reaches into and engages with the pump channel formed in the pump module for example as a trench in a housing part of the pump module. Via the engagement, the wobbling device automatically is laterally aligned with respect to the pump module.

In one embodiment, the pump module comprises a housing part and a flexible wall section together forming a pump channel to which a fluid is to be pumped. The wobbling device herein is constituted to act onto the flexible wall section for locally depressing the flexible wall section, for example a membrane, in order to pump a fluid through the pump channel.

The pump channel advantageously is formed by a trench in the housing part of the pump module. The housing part may be made for example of a rigid plastic material. The flexible wall section in turn may for example be formed by a membrane attached to the housing part, or by a thin wall section having a sufficient elasticity and formed in one piece with the housing part, for example using a two-component molding technique.

The pump channel may for example extend along an arc of a circle, wherein the circle is not closed, but interrupted to separate an inlet at a first end of the pump channel from an outlet at a second end of the pump channel. The pump channel may for example extend along a plane transverse to the vertical direction. The pump channel hence is laid out in a horizontal plane, and the flexible wall section of the pump channel is depressed vertically to that horizontal plane in order to perform a peristaltic pump action on the pump channel.

The idea underlying the invention shall subsequently be described in more detail with regard to the embodiments shown in the figures. Herein, FIG. 1 shows a schematic view of an infusion device in the shape of a peristaltic (volumetric) infusion pump;

FIG. 2 shows a top view of an embodiment of a disposable pump module;

FIG. 3A shows a sectional, explosive view of a pump module along line A-A according to FIG. 2, together with a wobbling device of a first type;

FIG. 3B shows a sectional, explosive view of the pump module along line A-A according to FIG. 2, together with a wobbling device of a second type;

FIG. 4A shows a sectional view of the pump module along line A-A according to FIG. 2 in interaction with the wobbling device of the first type;

FIG. 4B shows a sectional view of the pump module along line A-A according to FIG. 2 in interaction with the wobbling device of the second type;

Figure 1:
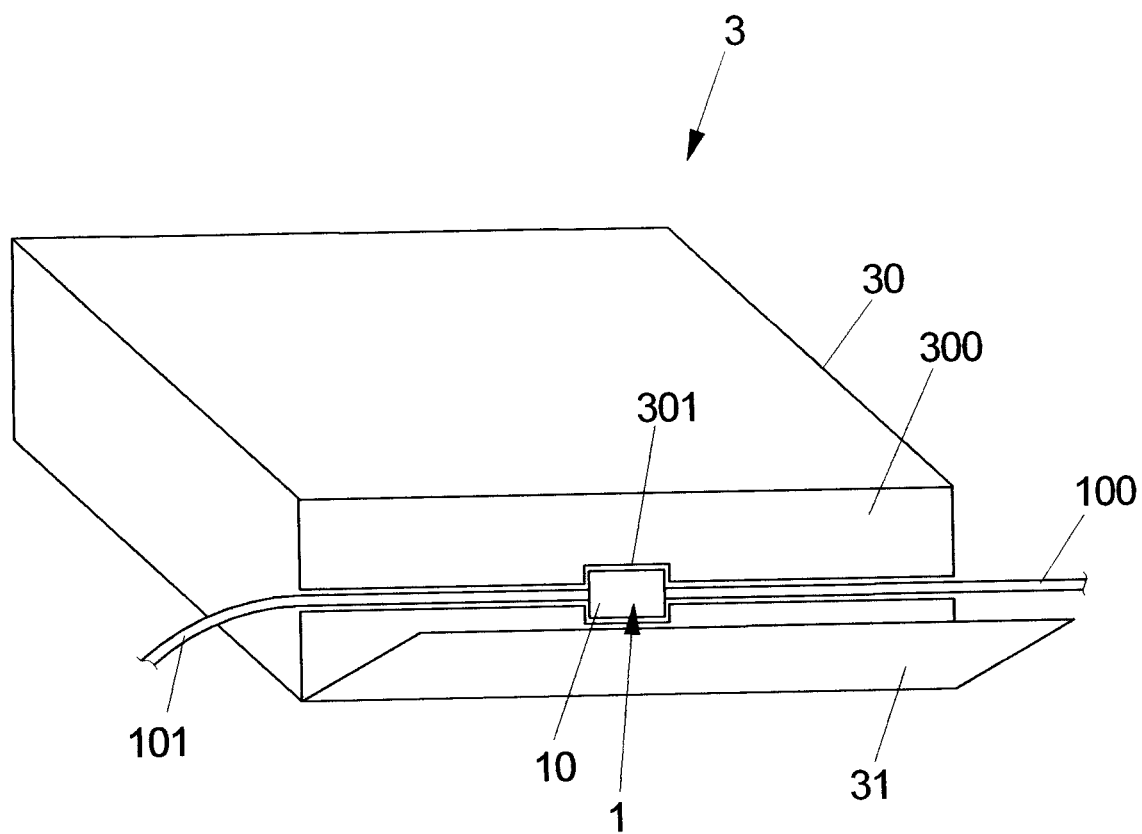

FIG. 1 shows in a schematic view an infusion device 3 in the shape of a peristaltic (volumetric) infusion pump. The infusion device 3 comprises a housing 30 having a front face 300 and a receptacle 301 arranged on the front face 300. The receptacle 301 is shaped as a reception opening and is constituted to receive a pump module 1.

Attached to the housing 30 is a door 31 which may be pivoted with respect to the housing 30 for accessing the front face 300 and the receptacle 301 arranged thereon. By pivoting the door 31 away from the front face 300, the receptacle 301 may be accessed for inserting a pump module 1 into the receptacle 301 or for removing the pump module 1 from the receptacle 301. During operation of the infusion device 3, the door 31 is closed such that the pump module 1 is securely held in the receptacle 301.

FIG. 2 shows a schematic top view of a disposable pump module 1 which may be part of an infusion set to be attached to the infusion device 3. The pump module 1 comprises a housing 10 having an inlet 100 and an outlet 101. The inlet 100 and the outlet 101 may be connected to a suitable tubing forming an infusion line such that an upstream flow U may enter the pump module 1 at the inlet 100 and a downstream flow D may exit the pump module 1 through the outlet 101.

Within the pump module 1 a flow path L is defined through which fluid may pass the pump module 1. Along the flow path L, as viewed from the inlet 100, a fluid flow first passes a pressure sensing location 11, then through an end 120A enters a pump channel 121 and exits the pump channel 121 through an end 120B, and flows through another pressure sensing location 13.

At the pressure sensing locations 11, 13 thin, flexible wall sections on the housing 10 may be provided such that pressure sensors of the infusion device 3 are enabled to sense the pressure at the pressure sensing locations 11, 13 on the flow path L.

In the embodiment of the pump module 1 according to FIG. 2, the pump channel 121 has the shape of an arch of a circle. The circle is not circumferentially closed such that the ends 120A, 120B of the pump channel 121 are separated from one another.

As visible from FIG. 3A, 3B and FIG. 4A, 4B, the pump channel 121 is formed by a trench in a housing part 103 of the housing 10 of the pump module 1. The pump channel 121, towards the outside, is covered by a flexible wall section 12 in the shape of a membrane, which is held between the housing part 103 and another, top housing part 102. The flexible wall section 12 may be glued or welded to the housing part 103 or may be held in-between the housing parts 102, 103 in a clamping fashion. The flexible wall section 12 may alternatively be formed in one piece together with the housing parts 102, 130 using for example a two-component molding technology.

Whereas the flexible wall section 12 is elastic such that it may locally be depressed in order to perform a pump action, the housing parts 102, 103 are formed as rigid pieces for example from plastics.

FIG. 3A, 4A and FIG. 3B, 4B show the pump module 1 in interaction with different types of wobbling devices 20 of a pump actuation mechanism 2. The wobbling devices 20 comprise a wobbling disc 200 and an arched projection 201 projecting from the wobbling disc 200 through an opening 104 in the top housing part 102 towards the flexible wall section 12 and, along the pump channel length, forming an arch similar in shape to the arch of the pump channel 121.

In an operational state of the infusion device, as shown in FIGS. 4A and 4B, each wobbling device 20 is in abutment with a projecting rim 122 of the flexible wall section 12 of the pump module 1. The wobbling device 20 herein is pretensioned towards the flexible wall section 12. This leads to a preloading of the flexible wall section 12, causing the wobbling device 20 to be in abutment with the flexible wall section 12 along the entire channel length of the pump channel 121 such that the flexible wall section 12 is preloaded along the channel length of the pump channel 121.

By means of the wobbling device 20 fluid may be pumped through the pump channel 121 between the inlet 100 and the outlet 101. The wobbling device 20, during operation of the infusion device 3, is driven to perform a wobbling action about a rotational axis A such that the wobbling device 20, by means of its projection 201, locally depresses the flexible wall section 120 at a depression location, the depression location revolving in a tumbling direction R about the rotational axis A along the channel length of the pump channel 121. By the local depression of the flexible section 120, the pump channel 121 is locally squeezed off, and by the revolving action of the wobbling device 20 fluid is peristaltically pumped through the pump channel 121 in the tumbling direction R.

The wobbling disk 200 of the wobbling device 20 extends along a plane perpendicular to a tumbling axis A', which is arranged at a skew angle relative to the rotational axis A. During operation of the infusion device 3, the wobbling disk 200 performs a tumbling motion T, and the tumbling axis A' revolves about the rotational axis A, wherein the rotational position of the tumbling device 20 remains stationary.

The tumbling device 20 of FIG. 3A, 4A and the tumbling device of FIG. 3B, 4B differ in the shape of the projection 201. The tumbling device 20 of FIG. 3A, 4A comprises a projection 201 having a rounded outer edge acting onto the rim 122 of the flexible wall section 120. The projection 201' of the wobbling device 20 of FIG. 3B, 4B, in contrast, is flat at its face pointing away from the wobbling disk 200, and via its flat circumferential face acts onto the rim 122 of the flexible wall section 120.

The embodiment of the wobbling device 20 of FIG. 3A, 4A is self-aligning in that it allows for a self-alignment of the lateral position of the wobbling device 20 with respect to the pump channel 121 formed in the pump module 1. When the wobbling device 20 by means of its projection 201 engages with the pump channel 121 as shown in FIG. 4A on the left, the wobbling device 20 will automatically find its position with respect to the pump module 1 such that an optimum depression of the flexible wall section 120 becomes possible.

The self-alignment of the wobble device 20 becomes possible when the wobble device 20, by at least some margin, is laterally displaceable with respect to the pump module 1, as will be described below with respect to the embodiment of FIGS. 6 to 8.

In contrast to the embodiment of FIG. 3A, 4A, the wobble device 20 of the embodiment of FIG. 3B, 4B is not self-aligning, because the flat face of the projection 201' does not cause a lateral alignment of the wobbling device 20 with respect to the pump module 1 as the projection 201', as visible from FIG. 4B, does not engage with the pump channel 121 (i.e., it does not reach into the pump channel 121).

Figure 5A:
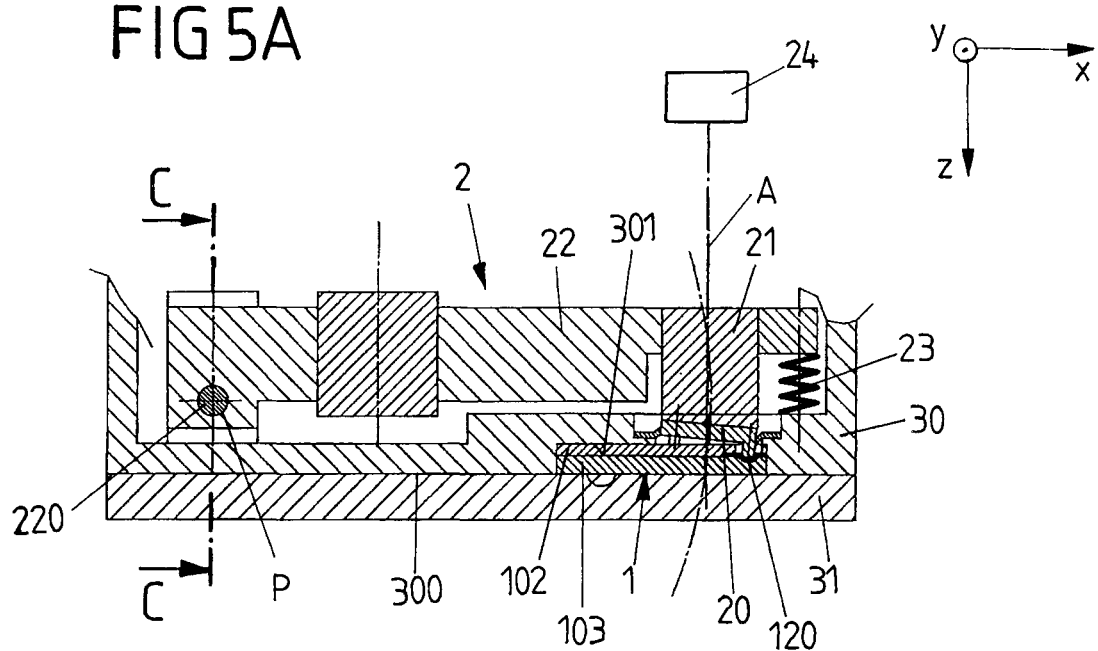
FIG. 5A shows a sectional view of an embodiment of an infusion device, including a pump actuation mechanism for driving the wobbling device, along a sectional line corresponding to line B-B according to FIG. 2.
Figure 5B:
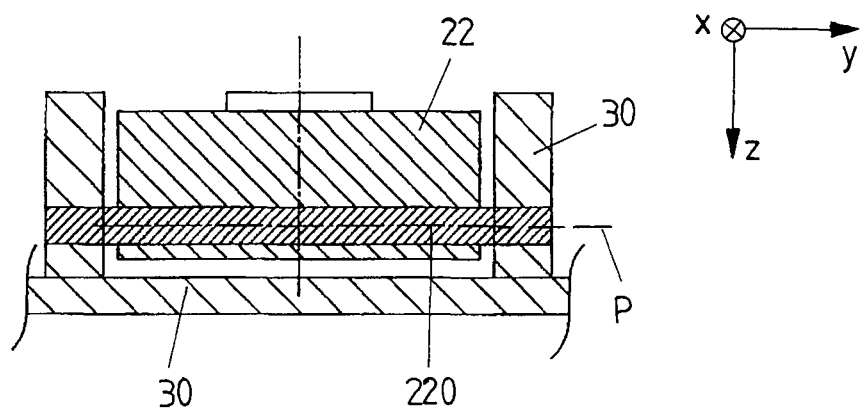
FIG. 5B shows a sectional view along the line C-C according to FIG. 5A.

The wobbling device 20—in the embodiment of FIG. 3A, 4A or FIG. 3B, 4B—is part of a pump actuation mechanism 2, as it is shown in FIG. 5A.

The pump actuation mechanism 2 comprises a drive shaft 21 which is rotatably mounted about a rotational axis A on a carrier element 22. The drive shaft 21 is driven by a drive device 24 in the shape of an electric motor, wherein a suitable gearing in-between the drive device 24 and the drive shaft 21 may be provided for driving the drive shaft 21. The carrier element 22 is mounted on the housing 30 of the infusion device 3 in a pivotable fashion and for this is pivotable about a pivot axis P via an axis 220.

By pivoting the carrier element 22 about the pivot axis P, the longitudinal position of the wobbling device 20 along the rotational axis A can be adapted. The carrier element 22 herein is pretensioned by means of a spring element 23 in the shape of a tension spring in a vertical direction Z towards a pump module 1 placed in the receptacle 301 on the front face 300 of the housing 30. By means of the pre-tensioning, hence, the wobbling device 20 is brought into abutment with the flexible wall section 12 of the pump module 1 such that the flexible wall section 12 is elastically preloaded.

Because the distance between the pivot axis P and the rotational axis A is large, the wobbling device 20 is substantially displaceable along the vertical direction Z with respect to the pump module 1. Because the axis 220 is stiff, the wobbling device 20 herein is not displaceable in a direction transverse to the rotation axis A with respect to the receptacle 301 on the front face 300 of the housing 30.

Figure 6:
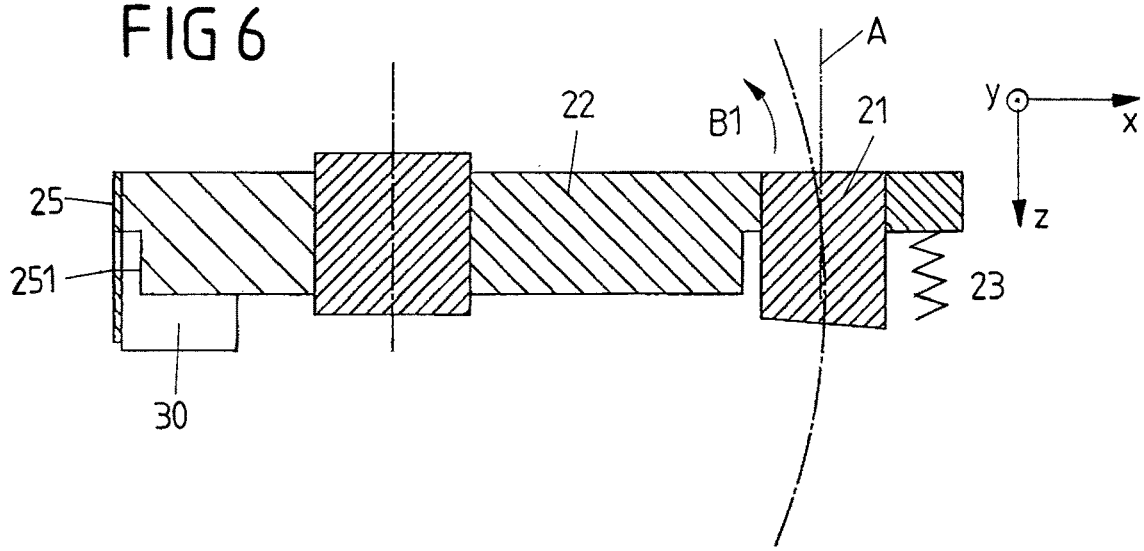
FIG. 6 shows a view of another embodiment of a pump actuation mechanism.
Figure 7A:
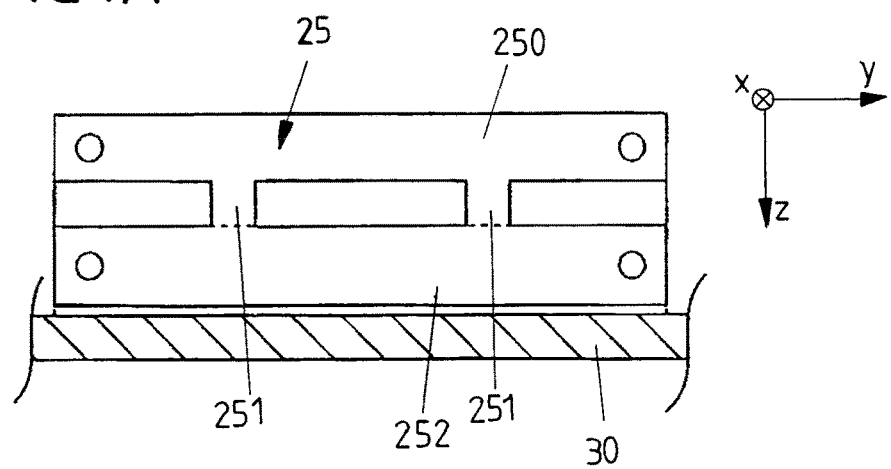
FIG. 7A shows an example of a connection element for connecting a carrier element of the pump actuation mechanism with a housing element.
Figure 7B:
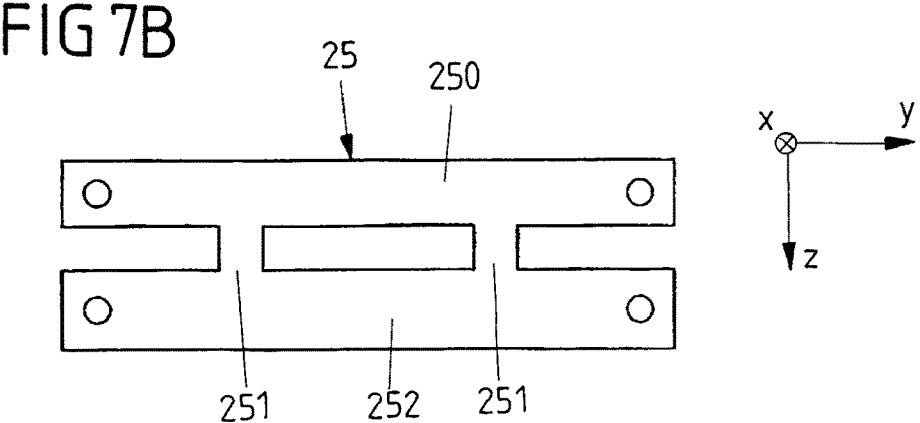
FIG. 7B shows a separate view of a connection element example.
Figure 8:
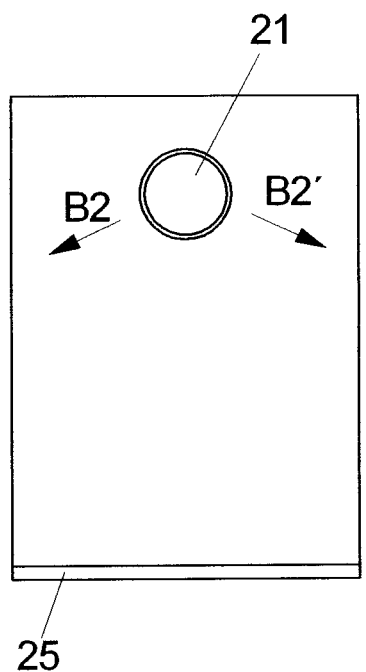
FIG. 8 shows a top view of the pump actuation mechanism.

An embodiment implementing the instant invention is shown in FIGS. 6 to 8. In this embodiment, the carrier element 22 is connected to the housing element 30 via a connection element 25 which is by at least some margin deformable such that the lateral position of the carrier element 22 is, to at least some degree, displaceable in a plane transverse to the rotational axis A, i.e. in a plane spanned by the horizontal directions X, Y.

The connection element 25 comprises a connection section 250 fixedly connected to the carrier element 22 and a connection section 252 fixedly connected to the housing element 30. The connection sections 250, 252 are integrally connected by means of elastic connecting webs 251, which are bendable to allow for a lateral displacement of the carrier element 22 along bending directions B2, B2' in the horizontal plane spanned by the horizontal directions X, Y, as shown in FIG. 8. In addition, the connection element 25 is bendable in a bending direction B1 as shown in FIG. 6 to allow for a vertical displacement of the wobbling device 20 along the vertical direction Z.

The position of the carrier element 22 hence is adjustable with two degrees of freedoms, namely by bending the connection element 25 in the bending direction B1 as indicated in FIG. 6 (to allow for a displacement of the wobbling device 22 along the vertical direction Z) and along the bending directions B2, B2' as indicated in FIG. 8 (to allow for a lateral displacement of the wobbling device 20 with respect to the vertical direction Z). The position of the wobbling device 20 with respect to the pump module, hence, is adjustable laterally within the plane of the front face 300 on which the receptacle 301 is arranged, namely along the plane spanned by the directions X, Y perpendicular to the vertical direction Z.

In particular, when the wobbling device 20 is self-aligning as in the embodiment of FIG. 3A, 4A, the wobbling device 20 hence may find its optimum position with respect to the pump module 1 automatically when inserting the pump module 1 into the receptacle 301. Once the wobbling device 20 by means of its projection 201 engages with the pump channel 121, the carrier element 22 is laterally displaced by deforming the connection element 25 (by subjecting the connection element 25 to torsion). Tolerances in the pump module 1 and in the pump actuation mechanism 2 hence may be overcome, and an optimum engagement of the wobbling device 20 with the pump channel 121 of the pump module 1 may be achieved, leading to an increased flow rate accuracy during operation of the infusion device 3.

Figure 9:
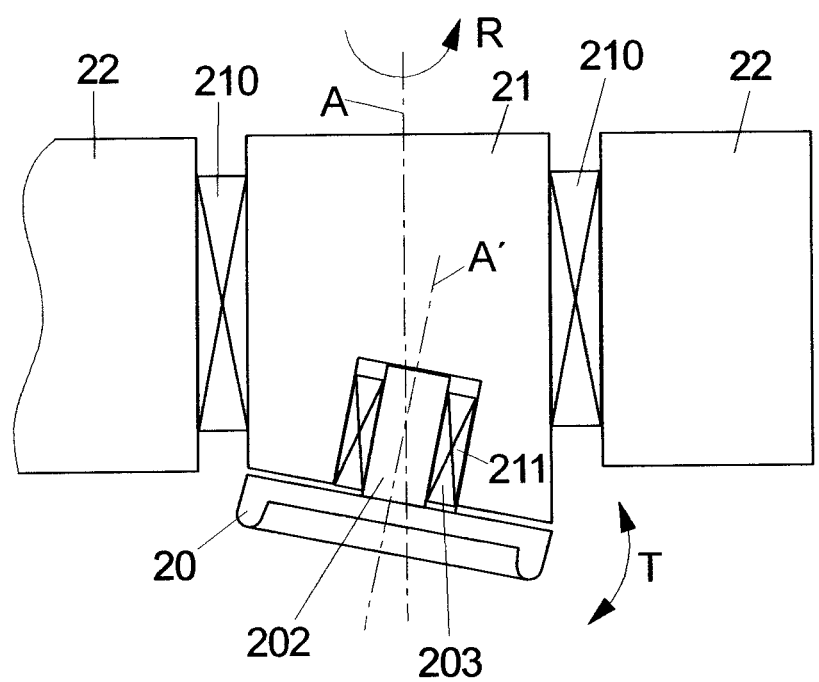
FIG. 9 shows a schematic view of the connection of the wobbling device with a drive shaft of the pump actuation mechanism.

FIG. 9 shows the mounting of the wobbling device 20 on the drive shaft 21 and the mounting of the drive shaft 21 on the carrier element 22. The wobbling device 20 is mounted on the drive shaft 21 by means of a first bearing 203 arranged between a pin 202 of the wobbling device 20 and a circumferential face of a bearing opening 211 provided in the drive shaft 21. By means of the bearing 203 the wobbling device 20 is rotatable about the tumbling axis A' with respect to the drive shaft 21. The drive shaft 21 in turn is mounted via a bearing 210 on the carrier element 22 such that it is rotatable with respect to the carrier element 22 about the rotational axis A. When driving the drive shaft 21 via the drive device 24, the drive shaft 21 is rotated about the rotational axis A relative to the carrier element 22. This causes the bearing opening 211 to rotate about the rotational axis A such that the wobbling device 20 is forced into a tumbling motion T about the rotational axis A in that the tumbling axis A' revolves about the rotational axis A. The wobbling device 20 herein remains rotationally fixed (and hence is not rotated), but performs a tumbling motion T and hence, in a revolving fashion, acts onto the flexible wall section 12 of the pump module 1 to peristaltically pump a fluid through the pump channel 121.

Because the wobbling device 20 is mounted on the drive shaft 21 and the drive shaft 21 is mounted on the carrier element 22, the wobbling device 20 is laterally displaced together with the carrier element 22. Upon engaging of the projection 201 with the pump channel 121, the lateral position of the wobbling device 20 hence is self-aligned with respect to the pump module 1, causing a deformation of the connection element 25 and hence an adjustment of the lateral position of the carrier element 22.

The idea underlying the invention is not limited to the embodiments described above, but may be implemented in an entirely different fashion.

In particular, the wobble device may have an entirely different shape. Likewise, the pump module may have a different structure and shape. Also, the structure and mechanics of the pump actuation mechanism may be implemented in a different fashion.

LIST OF REFERENCE NUMERALS

1 Pump module
10 Housing

100 Inlet
101 Outlet
102, 103 Housing part
104 Opening
11 Pressure sensing location
12 Flexible wall section (membrane)
120A, 120B End
121 Pump channel
122 Rim
13 Pressure sensing location
2 Pump actuation mechanism
20 Wobbling device (wobbling device)
200 Wobbling disc
201, 201' Projection
202 Pin
203 Bearing
21 Drive shaft
210 Bearing
211 Bearing opening
22 Carrier element
220 Axis
23 Spring element
24 Drive motor
25 Connection element
250 Connection section
251 Connecting webs
252 Connection section
3 Infusion device
30 Housing element
300 Front face
301 Receptacle
31 Door
A Rotational axis
A' Tumbling axis
B1, B2, B2' Bending direction
D Downstream flow
L Flow path
P Pivot axis
R Tumbling direction
T Tumbling movement
U Upstream flow
X, Y, Z Direction

The invention claimed is:

1. An infusion device, comprising:
a housing element having a receptacle for receiving a pump module, and
a pump actuation mechanism having a wobbling device arranged on the housing element and a drive shaft being rotatable about a rotational axis, wherein the wobbling device is actuatable, by rotating the drive shaft about the rotational axis, to perform a tumbling motion about the rotational axis with respect to the receptacle for acting onto the pump module received in the receptacle in order to pump a fluid through the pump module,
the pump actuation mechanism having a carrier element connected at a first end to the housing element via a hinge and at a second, opposite end to the housing element via a spring, the wobbling device and the drive shaft being disposed at the second end of the carrier element.

2. The infusion device according to claim 1, wherein the wobbling device is displaceable along the rotational axis with respect to the receptacle and is elastically pretensioned with respect to the housing element along the rotational axis in a direction pointing towards the receptacle.

3. The infusion device according to claim 1, wherein the wobbling device is mounted on the drive shaft via a first bearing such that the wobbling device is actuated to perform a tumbling motion when rotating the drive shaft.

4. The infusion device according to claim 3, wherein the drive shaft is mounted on the carrier element via a second bearing such that the drive shaft is rotatable with respect to the carrier element about the rotational axis.

5. The infusion device according to claim 4, wherein the carrier element is mounted on the housing element such that the carrier element is displaceable along at least one direction transverse to the rotational axis with respect to the housing element.

6. The infusion device according to claim 4, wherein the carrier element is connected to the housing element via the hinge in the form of an elastically deformable connection element.

7. The infusion device according to claim 4, wherein the carrier element is elastically pretensioned with respect to the housing element along the rotational axis.

8. The infusion device according to claim 1, wherein the wobbling device comprises a wobbling disc extending along a plane transverse to a tumbling axis, wherein the tumbling axis is arranged at a skew angle with respect to the rotational axis and tumbles about the rotational axis when the wobbling device is driven by the drive shaft.

9. The infusion device according to claim 8, wherein the wobbling device comprises a protrusion protruding from the wobbling disc along the tumbling axis for acting onto the pump module.

10. The infusion device according to claim 1, wherein the wobbling device is constituted to self-align itself with respect to the pump module along at least one direction transverse to the rotational axis when acting onto the pump module during operation of the infusion device.

11. The infusion device according to claim 1, wherein the pump module comprises a housing part and a flexible wall section together forming a pump channel through which a fluid is to be pumped, wherein the wobbling device acts onto the flexible wall section for locally depressing the flexible wall section in order to pump a fluid through the pump channel.

12. The infusion device according to claim 11, wherein the pump channel is formed by a trench in the housing part of the pump module.

13. The infusion device according to claim 11, wherein the pump channel extends along an arc of a circle.

14. The infusion device according to claim 11, wherein the pump channel extends along a plane transverse to the rotational axis.

* * * * *